United States Patent [19]
Fleisher et al.

[11] Patent Number: 5,221,756
[45] Date of Patent: Jun. 22, 1993

[54] METHOD FOR THE RECOVERY AND PURIFICATION OF MALTOL

[75] Inventors: Alexander Fleisher, Wayne, N.J.; Richard J. Coleman, Stamford, Conn.; Guy J. Gloor, Trenton Falls; Yan Gorenshteyn, Edgewater, both of N.J.

[73] Assignee: Florasynth, Inc., New York, N.Y.

[21] Appl. No.: 839,916

[22] Filed: Feb. 21, 1992

[51] Int. Cl.$^5$ .......................................... C07D 309/40
[52] U.S. Cl. ................................................... 549/418
[58] Field of Search ......................................... 549/418

[56] References Cited

U.S. PATENT DOCUMENTS 3,501,501  3/1970  Heintz et al. ...................... 549/418

OTHER PUBLICATIONS

Fleisher and Fleisher, "Water-Soluble Fractions of the Essential Oils", *Perfumer and Flavorist*, vol. 16, May/-Jun., pp. 37–41, 1991.

Goos and Reiter, "New Products from Wood Carbonization", *Industrial and Engineering Chemistry* vol. 38, No. 2, pp. 132–135, Feb. 1946.

LeBlanc and Akers, "Maltol and Ethyl Maltol From the Larch Tree to Successful Food Additive", *Food Technology*, pp. 78–84, Apr. 1989.

*Primary Examiner*—Nicky Chan
*Attorney, Agent, or Firm*—Scully, Scott, Murphy & Presserg310103

[57] ABSTRACT

Pure maltol is recovered from maltol containing mixture by co-distillation with an aliphatic or cylcloaliphatic hydrocarbon or hydrocarbon mixture in which the maltol is substantially insoluble.

7 Claims, 1 Drawing Sheet

Figure
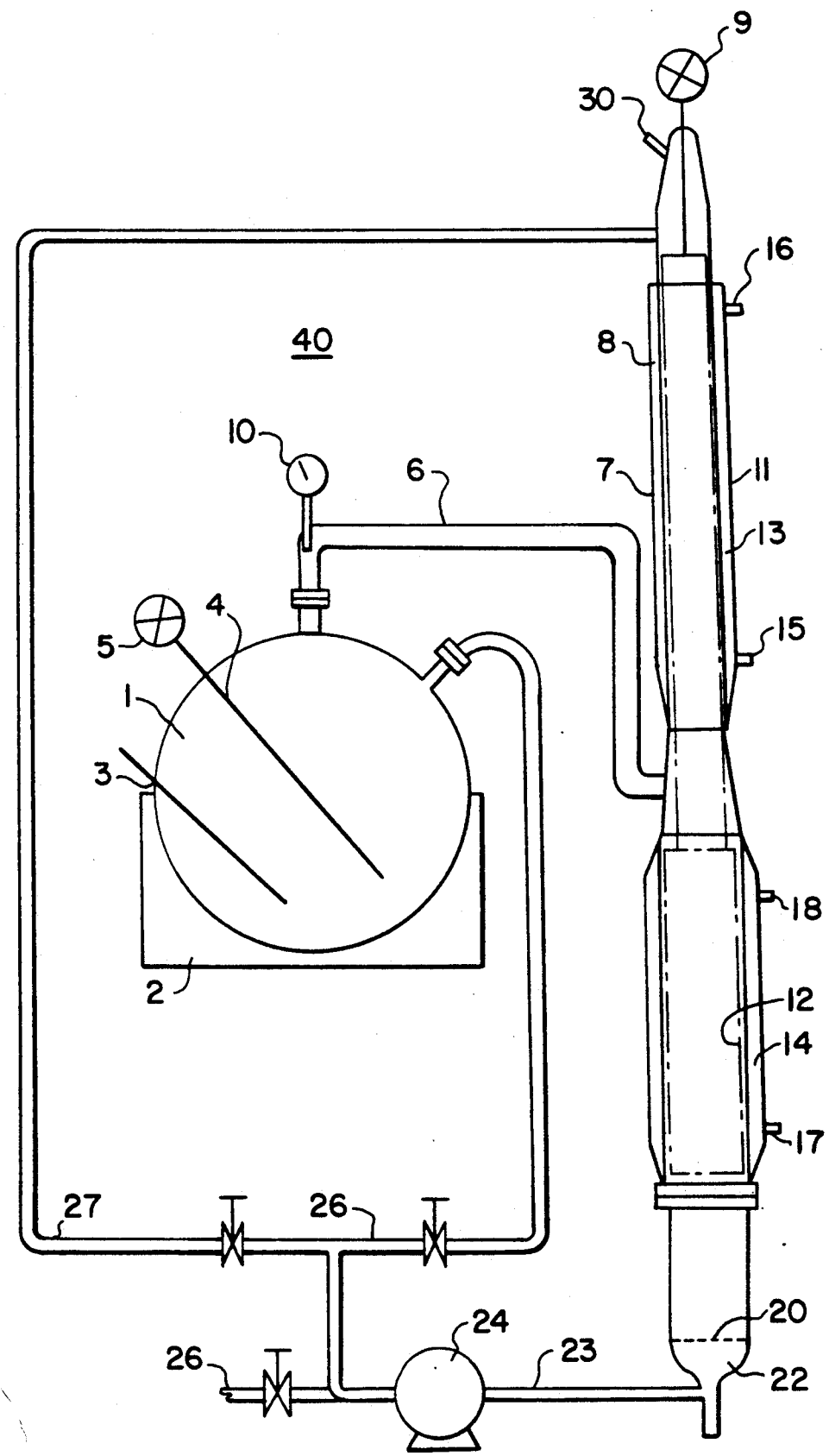

METHOD FOR THE RECOVERY AND PURIFICATION OF MALTOL

FIELD OF THE INVENTION

This invention is related to a process FOR OBTAINING maltol and more particularly to a process for obtaining pure maltol.

DESCRIPTION OF THE PRIOR ART

Maltol (2-methyl-3-hydroxy-4-pyrone) is a heterocyclic aroma chemical used extensively in flavor and fragrance compositions. It is naturally occurring in numerous plant species, especially in coniferous trees such as Larix and Abias spp.

The presence of maltol in various plant sources has been known for many years and considerable efforts have been made to develop a sensible method for its commercial recovery. The existing techniques are, however, rather complex and the use of the resulting maltol is cost-prohibitive.

Heintz, et al., U.S. Pat. No. 3,501,501, teaches the purification of crude maltol by its co-distillation with ethylene glycol.

The solubility of maltol in ethylene glycol at ambient temperatures exceeds 4%. This completely prohibits economical maltol recovery from dilute mixtures, effectively eliminating virtually all natural sources. Moreover, there is a limiting practical consideration being that the crystallization of maltol from ethylene glycol at ambient temperatures is very slow. At very low temperatures the viscosity of ethylene glycol also considerably hampers filtration of maltol from ethylene glycol/maltol mixtures.

Ethylene glycol derived maltol is also unsuitable for food application, since the removal of toxic ethylene glycol contamination from maltol is rather difficult.

Maltol can be obtained in very small amounts from the destructive distillation products of wood, and by a partially synthetic process from kojic acid, which is obtained from fermentation media. However, maltol, obtained therefrom, is still quite expensive.

Maltol has been reported to be in the bark of some species of larch trees. Maltol is present in larch bark in combined form to an extent varying from about 0.1 percent to about 2 percent by weight depending upon the bark layer and the season of harvest. The richest supply of maltol is found in the bark of roots of the larch trees although, for practical reasons, not much root bark is harvested. Large quantities of larch trees and bark containing maltol exist and are available primarily in the northwest part of the United States and southwest Canada. The bark is available at sawmills where it is stripped off of larch trees and stored in a pile, there to be burned for fuel or otherwise used if economical processes for recovering useful components therefrom can be found.

Fleisher & Fleisher, "Water-Soluble Fractions of the Essential Oils", *Perfumer and Flavorist*, Vol. 16, May/June, pp. 37 to 41, 1991, gives the composition and details of recovery of compounds from fir needles (*Abias balsamea* L.) and a good bibliography of literature discussing recovery of essential oils.

Goos and Reiter, "New Products from Wood Carbonization", *Industrial and Engineering Chemistry*, Vol. 38, No. 2, pp. 132 to 135, February 1946, discloses the isolation of maltol in small amounts by fractional distillation of soluble tar fractions.

LeBlanc and Akers, "Maltol and Ethyl Maltol From the Larch Tree to Successful Food Additive", Food Technology, pp. 78 to 84, April 1989, gives a survey of the history production, properties and applications of maltol and ethyl maltol.

The present invention provides a totally natural, environmentally sound, efficient process for the recovery and purification of maltol without large expenditures in equipment or materials. Furthermore, it provides a means by which natural maltol may be produced in commercial quantities in a substantially pure state.

SUMMARY OF THE INVENTION

According to the present invention maltol is efficiently separated from maltol-containing mixtures by co-distillation with a liquid hydrocarbon in which maltol is poorly soluble and which is distillable without degradation at reasonable temperatures.

The liquid hydrocarbon can be an aliphatic or cycloaliphatic hydrocarbon each of which can be saturated or unsaturated, i.e. contain ethylenic bonds. The aliphatic hydrocarbons can be branched or straight chained hydrocarbons. These hydrocarbons are normally liquid at room temperature and, in general distill at temperatures in excess of 120° C. at atmospheric pressure. The cycloaliphatic hydrocarbons include bicyclic hydrocarbons as exemplified by the terpenes. The preferred cyclic hydrocarbons are naturally-occurring terpenes such as alpha-pinene, beta-pinene, and limonene. Mixtures of the hydrocarbons can be used in the present process, but it is usually preferred to use a single hydrocarbon which permits more facile control of the process.

Crude maltol is obtained from any natural source, usually by solvent extraction followed by concentration of the maltol extract under conditions which do not degrade the crude mixture. The crude mixture is then distilled with the hydrocarbon to recover substantially pure maltol crystals which can be further purified if desired.

BRIEF DESCRIPTION OF THE FIGURE

The FIGURE shows a distillation apparatus for recovering pure maltol from crude maltol mixtures using a liquid hydrocarbon which is distilled with the maltol. Hereinafter, the invention will be described using maltol but it should be understood that the description is to a degree applicable to the recovery and purification of ethyl maltol.

BRIEF DESCRIPTION OF THE INVENTION

There is shown in the FIGURE a purification system 40 which consists of a flask or other vessel 1 capable of withstanding full vacuum while being heated. The flask is provided with a source of heat 2 which may be electrical heating jackets, a hot oil or liquid bath or other known heating means capable of heating the contents of the flask to at least 180° C. The flask is provided with a temperature measuring device such as a thermometer 3, or thermocouple and an agitator 4 driven by a suitable motor 5. The flask 1 is connected by glass tubing 6 to a condenser generally shown as 7 which is equipped with a mechanical scraper 8 driven by motor 9. A pressure gauge 10 is provided to measure the system pressure (vacuum).

The condenser may be a single or multiple stage condenser. Herein is shown a two stage condenser having condensing surfaces 11 and 12 which are cooled using cooling jackets 13 and 14, respectively. Cold water from a chiller (not shown) enters the jacket 13 at 15 and exits at 16 while it enters jacket 14 at 17 and exits at 18. The condenser 7 is equipped with a filter 20 used to separate the maltol from the hydrocarbon. The filter 20 may be part of the condenser or may be a separate filter connected to the condenser by suitable piping. The lower portion of the condenser 22, beneath the filter is connected by piping 23 to a pump 24 used to recirculate hydrocarbon to either the flask 1 or condenser 7 or to recover the hydrocarbon at 26.

A source of vacuum is not shown but is connected to the condenser at 30. To produce high quality maltol, it is preferable that all the wetted surfaces of the apparatus be fabricated from glass, teflon or other inert substances.

In operation of the system 40, a crude maltol is placed in the flask 1 with from 5 to 30 times its weight of a liquid hydrocarbon in which it is substantially insoluble and the mixer 4 turned on to distribute the maltol in the liquid. A vacuum of about 17 inches mercury is pulled on the system and the hydrocarbon heated at about 140° to 160° C. to initiate distillation of maltol and hydrocarbon to the condenser 7. Immediately crystals of maltol form on the crystallizer surfaces 11 and 12 which are wiped clean by the revolving scraper 8 causing the maltol to fall into the filter 20. Hydrocarbon is collected below the filter at 22 and returned using pump 24 through glass tubing 26 to the flask. If desired, a portion of the hydrocarbon may be pumped through glass tubing 27 to the top of the condenser to wash the vapors being, distilled over through line 6 and to further remove maltol scrapped from the condenser walls.

A vacuum of from 1-28 inches of mercury or greater may be employed, preferably 10 inches or greater and more preferably 15 inches of mercury or more. Usually a vacuum of 17 inches of mercury is used to maintain the flask temperature around 150° C. when using terpenes as a solvent. The vacuum will depend on the solvent used while maintaining the flask temperature below 180° C, preferably below 160° C. to prevent burning or heat destruction of maltol or the crude components present with unpurified maltol.

The hydrocarbon employed in this invention is a liquid boiling at atmospheric pressure and temperatures of 100° C. or more. It is a hydrocarbon in which maltol is essentially insoluble.

A simple test procedure can be employed to determine suitable hydrocarbon solvents. The hydrocarbon solvents are those which, on co-distillation, are capable of carrying maltol from natural sources to be condensed along with the solvent on a cooling surface. The test procedure merely involves co-distilling a mixture of the selected solvent with the maltol source and condensing vapors produced by the distillation. If maltol is carried during the distillation, white crystals will form on the condensing surface. The distillation apparatus conveniently can be any simple laboratory set-up useful for distilling small quantities of liquid.

The hydrocarbon is preferably an aliphatic, saturated or unsaturated, straight or branch chain or cycloalkane or alkene preferably of from 8 to 14 carbons. Suitable hydrocarbons include nonene, octane, dodecane, decane, undecane and terpenes including alpha pinene, beta pinene and limonene. It is preferred to employ naturally occurring hydrocarbons such as terpenes that are obtained from balsam fir such as alpha-pinene, beta-pinene and limonene and the like which are natural and food approved. The chief characteristic of the hydrocarbon is that it be economical, naturally occurring and that maltol not be appreciably soluble i.e. less than 1.0% at 25° C. in the hydrocarbon, preferably less than 0.1% at 25° C.

The crude resin obtained from fir trees normally contains 3 to 5% maltol. The resin is dispersed in from 10:1 to 20:1 ratio of hydrocarbon to maltol in the agitated flask. The temperature of the flask is raised to below about 160° C, preferably 100° C.-160° C. and more preferably from about 120 to about 160° C., even more preferably about 120 to about 150° C.

The dispersant hydrocarbon and maltol containing resin mixture or suspension is subjected to sufficient vacuum to maintain the temperature within the previous limits depending on the boiling point of the hydrocarbon employed. The maltol is distilled with the hydrocarbon vapor at a temperature of about 110 to about 140° C.

Once the maltol has been substantially distilled over to the crystallizer and recovered, the hydrocarbon is removed and the crystals blown free of hydrocarbon prior to removal from the filter. The crystals are removed from the filter and dried or can be co-distilled with more hydrocarbon or otherwise further purified as by crystallization if desired. The process of this invention is so selective that no further purification is normally needed.

The following examples are provided to further illustrate the invention:

EXAMPLE 1

1200 ml of alpha-pinene and 100 g of technical maltol (85 to 90% pure) were added to a flask fitted with a glass distilling head connected to another flask which was maintained in an ice bath.

The first flask was heated with the entire system under vacuum. The vacuum was maintained such that the vapor temperature was constantly 125 to 130° C. White crystals were noticed immediately upon condensation of the liquid in the chilled flask. After approximately 900 ml of distillate were collected the crystals were removed from the distillate by filtration and the liquid returned to the heated flask. Repetition of this process four times and combination of the resultant crystals filtered from the distillate showed them to be a nearly quantitative yield of essentially pure maltol.

EXAMPLE 2

6000 g of Fir Balsam oleoresin derived from the solvent extraction of *Abias balsamea* L. needles (FDA approved) was melted and placed in the flask of the apparatus shown in the FIGURE. 6.0 liters of alpha-pinene was poured into the crystallizer/filter. After allowing the pipework to fill, the level was measured and 1.5 liters of the alpha-pinene was pumped from the crystallizer/filter to the flask with the resin. The apparatus was evacuated to 17 to 17.5" Hg. vacuum and the resin flask was heated. Immediately upon distillation, white crystals were noticed in the condenser and the mechanical scraper was started to prevent them from collecting on the walls of the condenser. The recirculating pump was started and adjusted so that the rate of liquid being returned to the resin flask was approximately equal to the rate of distillate. A collection of white needle-like crystals rapidly began to collect on the glass filter.

The procedure was maintained for 4 hours over which time the rate of crystal formation gradually slowed to the point of being neglible. The pump was then stopped and the pinene distilled from the resin. The pinene was then removed from the crystallizer/filter. The crystals were blown free of pinene with air and then removed from the filter.

The resultant crystals were dried to remove further pinene and were found to weigh 268 g and be essentially pure maltol.

What is claimed is:

1. A method of recovery and/or purification of maltol comprising:
   heating a mixture of maltol under vacuum in a liquid hydrocarbon in which it is substantially insoluble to form a co-distillate of the hydrocarbon and the maltol; and
   condensing the co-distillate of hydrocarbon and maltol and recovering substantially pure crystals of maltol from the condensed mixture.

2. The method of claim 1 in which the hydrocarbon is an aliphatic or cycloaliphatic hydrocarbon.

3. The method of claim 2 in which the hydrocarbon is an alkane, alkene, cycloalkane or cycloalkene, containing from about 8 to about 14 carbon atoms.

4. The method of claim 3 in which the hydrocarbon is a terpene.

5. The method of claim 4 in which the terpene is a naturally occurring terpene selected from the group consisting of limonene, alpha-pinene and beta-pinene.

6. A method of recovery and/or purification of maltol comprising:
   a) heating a mixture of maltol in a natural terpene selected from the group consisting of alpha pinene, beta pinene, limonene and mixtures thereof, to a temperature of about 120° to about 160° under a vacuum of from about 10 to about 28 inches of mercury to form a co-distillate of terpene and maltol;
   b) condensing the co-distillate of maltol and terpene; and
   c) recovering substantially pure crystals of maltol from the distillate.

7. The method of claim 6 wherein the vacuum is from about 10 to about pb 20 inches of mercury.

* * * * *

UNITED STATES PATENT AND TRADEMARK OFFICE
CERTIFICATE OF CORRECTION

PATENT NO. : 5,221,756
DATED : June 22, 1993
INVENTOR(S) : Alexander Fleisher, et al.

It is certified that error appears in the above-indentified patent and that said Letters Patent is hereby corrected as shown below:

Title page, "Attorney, Agent, or Firm" "Scully, Scott, Murphy & Presserg310103" should read as --Scully, Scott, Murphy & Presser--

Column 1, line 6-7: "FOR OBTAINING" should read as --for obtaining--

Column 3, line 36: "scrapped" should read as --scraped--

Column 6, line 23, Claim 7: delete "pb"

Signed and Sealed this

Twelfth Day of April, 1994

Attest:

BRUCE LEHMAN

*Commissioner of Patents and Trademarks*

*Attesting Officer*